United States Patent [19]

Shanbrom

[11] Patent Number: 5,186,945
[45] Date of Patent: Feb. 16, 1993

[54] BLOOD PLASMA ANTIVIRAL PROCESS AND COMPOSITION

[76] Inventor: Edward Shanbrom, 2252 Liane La., Santa Ana, Calif. 92705

[21] Appl. No.: 433,540

[22] Filed: Nov. 7, 1989

Related U.S. Application Data

[63] Continuation-in-part of Ser. No. 321,522, Mar. 9, 1989, abandoned, and a continuation-in-part of Ser. No. 290,161, Dec. 28, 1988, Pat. No. 4,891,221, and a continuation-in-part of Ser. No. 276,113, Nov. 23, 1988, abandoned.

[51] Int. Cl.$^5$ .............................................. A61K 35/16
[52] U.S. Cl. .................................... 424/529; 424/530; 424/531; 424/533; 514/2
[58] Field of Search ................. 514/2, 6, 21; 424/529, 424/530, 531, 533

[56] References Cited

PUBLICATIONS

Itoh et al.–Chem. Abst. vol. 104 (1986) p. 141, 604C.
Ichikawa et al.–Chem. Abst. vol. 103 (1985) p. 115927v.
Ishida et al.–Chem. Abst. vol. 101 (1984) p. 221,998n.
Pompei et al.–Chem. Abst. vol. 93 (1980) p. 19069w.
Pompei et al.–Chem. Abst. vol. 92 (1980) p. 191170n.

*Primary Examiner*—Sam Rosen
*Attorney, Agent, or Firm*—Grant L. Hubbard

[57] ABSTRACT

The treatment of blood plasma to inactivate or destroy infective viruses, such as the cytomegalovirus CMV, by mixing the plasma with an effective amount of glycyrrhizic triterpenoid compounds is disclosed. Detergents, glycerol or ethylene diamine tetraacetic acid can be added to augment the affect of the glycyrrhizic triterpenoid compounds.

25 Claims, No Drawings

BLOOD PLASMA ANTIVIRAL PROCESS AND COMPOSITION

CROSS-REFERENCE TO RELATED APPLICATIONS

This is a continuation-in-part of my copending U.S. patent applications Ser. No. 07/321,522, filed Mar. 9, 1989, now abandoned, Ser. No. 07/290,161, filed Dec. 28, 1988, now U.S. Pat. No. 4,891,221, and Ser. No. 07/276,113, filed Nov. 23, 1988, now abandoned, to which priority is claimed.

FIELD OF THE INVENTION

This invention relates to the treatment of blood plasma with one or more of a class of compounds referred to here as glycyrrhizic compounds, exemplary of which are glycyrrhizin, glycyrrhizinic acid or glycyrrhetinic acid glycoside, and analogous triterpenes, e.g. carbenoxolone and cicloxolone and their derivatives, to inactivate viruses.

BACKGROUND OF THE INVENTION

Cytomegalovirus (CMV) is probably the most ubiquitous of the pathogenic viruses. Virtually all of the people living in the developing countries become infected with CMV early in life, and CMV infects over half the population in the developed countries of the world. CMV may remain essentially inactive in the body following an initial infection and may flare in to an active infection any time, most frequently when the body's immune system is compromised to a greater or lesser degree by disease, radiation or chemotherapy, drug therapy, surgical trauma, etc.

CMV is frequently associated with, and may be a causative or contributing factor in, life-threatening disease in individuals with suppressed immune systems, and can be a principal causative factor in pneumonia, neurological disorders, febrile illness, ocular disease and hepatitis. CMV infection is a serious limiting factor in the transplantation of organs, tissues and cells and the transfusion of blood and plasma from one individual to another. The kidney transplant patient runs a high risk of contracting serious, and not infrequently fatal, CMV infection from CMV introduced by the transplant organ. Recipients of whole blood, plasma, bone marrow, cornea, cardiac, and semen run a serious risk of CMV infectious disease, the risk being multiplied where the immune system of the recipient is suppressed to prevent rejection of the foreign organ or cells, or where immunosuppresion is present from natural causes.

CMV is frequently associated with *Pneumoncystis carinii* and may cause or contribute to encephalitis and colitis and may be associated with Kaposi's sarcoma in AIDS patients. CMV is so ubiquitous in the blood and organs of donors who, frequently, exhibit no symptoms of infection, and its direct and contributory effects in infectious diseases is so pervasive and subtle that a CMV infection is to be presumed if another causative agent cannot be established.

There are no proven cures or generally effective drugs for the treatment of CMV infections. Certain drugs, e.g. ganciclovir, has been shown to have limited effectiveness in the treatment of certain CMV infections, e.g. CMV retinitis, but has little effect in the treatment of CMV pneumonia. Live attenuated CMV vaccine has been developed but may not protect against infection by natural CMV, and there is a real risk that the attenuated CMV may reactivate during pregnancy and infect the fetus.

While a method of preventing, or even reducing the likelihood of transmitting CMV via transplant or transfusion organs, tissues, cells or fluids would be of enormous benefit to medical science, the present invention is not limited to treatments to inhibit CMV infection and is applicable to other classes of virus.

CMV is a member of the human herpesvirus (HV) group, which are responsible for much of mankind's discomfort and pain. The herpesviruses represent a very large, clearly defined group of viruses which are responsible for, or involved in, cold sores, shingles, a venereal disease, mononucleosis, eye infections, birth defects and probably several cancers. Three subfamilies are of particular importance. The alpha subfamily includes HV-1 (herpes virus simplex 1) which causes cold sores, fever blisters, eye and brain infections, HV-2 (herpes virus simplex 2) which cause genital ulceration, and HV-3 (HV varicella zoster) which causes chicken pox, shingles and brain infections. The beta subfamily includes HV-5, the principal member of which is CMV discussed above. The gamma subfamily includes HV-4 (Epstein-Barr) which causes infectious mononucleosis and is involved in Burkitt's lymphoma and nasopharyngeal carcinoma. Additional possibly pathogenic herpes viruses no doubt exist, one type of which, HV-6, of unknown pathogenicity has been identified. (Niederman, J. C. et al, The Lancet, Oct. 8, 1988, 817). There is evidence that the methods of this invention are effective in inhibiting the transmission of infections caused by many and perhaps all of the pathogenic herpes viruses.

While blood bankers have instituted rigid criteria for exclusion of potential donors in high risk categories, this is not a satisfactory solution to the most significant threat to face the health care community in many decades. Institution of HIV testing has blood products safer, but the complete elimination of HIV contaminated blood and blood products has not been possible using present knowledge and technology. The ELISA test, for example, misses approximately 1 in 200 (0.5%) HIV infected donors, and there is no certain method for excluding donor carriers of hepatitis, AIDS, and other infectious viruses. Increasing efforts are exerted to improve the safety of the blood supply such as retrovirus screening using surrogate markers, screening for HIV and other retroviruses with attention to population surveillance for newer agents, cleaner methods of extracting specific blood components by monoclonal antibody techniques and DNA methodologies, development of recombinant DNA products which by-pass the need for plasma derived clotting factors for administration to hemophiliacs. While careful screening of donors, followed by antibody testing reduces the risk of AIDS and other virus contaminated plasma, such methods require testing supplies and trained technicians which are not available and are too expensive for use in such places as central Africa and other third-world countries where AIDS infects up to one-third of the population. A simpler and less costly method of handling plasma is required in such areas of the world.

A photodynamic method has also been evaluated as a means of eradicating viral contaminants (Matthews J. L. et al, *Transfusion*, 28,1 1988) but has not been proved to be generally effective and safe. While donor-screened, heat-treated factor VIII products appear to be effective in protecting the hemophilia population, no methods are known to guarantee the safety of plasma. For the blood plasma recipient, however, the only reasonably reliable safety procedures are programs allowing for self donation prior to elective surgery by the donor and the use of plasma from designated donors, but such programs are incredibly difficult logistically. In spite of heroic efforts to meet the challenge of an AIDS-virus-contaminated plasma supply, an imperative need continues to exist for a method for treating blood plasma for use in transfusion. It is apparent from the foregoing discussion that a method of killing or inactivating pathogenic viruses in organs, tissues, cell and fluids intended for transfusion or transplantation would be an enormous advance in medicine. It is to this major national and worldwide health care challenge that the present invention is directed.

Licorice is a well-known flavoring agent. In addition to its use as a flavoring agent, licorice has long been a common folk medicine for the treatment of sore throats. While not widely known, various extracts of and preparations derived from licorice, e.g. glycyrrhizin and its derivatives, principally the salts of glycyrrhizic acid, have also been used to a limited degree for many years as an orally administered medication for the treatment of peptic ulcers (Chandler, R. F., Can. Pharm. J., V118, No.9, 1985), and oral administration of glycyrrhizin contemporaneously with saponin antiinflamatory agents has been reported to inhibit sapon and saponigen hemolysis (Segal, R. et al., Biochem. Pharmacol. 26, 7 1977).

The family of compounds of interest are, chemically, referred to as triterpenoids. The specific triterpenoids of interest are, principally, derived as extracts or derivatives of glycyrrhiza and are referred to here as GTPD compounds. GTPDs have been evaluated extensively in vitro, and have been administered orally, intramuscularly and intravenously. No significant toxicity from limited, short term administration of glycyrrhizin has been reported. Adverse reactions have been reported in certain instances of prolonged oral ingestion and a slight relapse after rapid discontinuation of intravenous administration of Stronger Neo-Minaphagen C (SNMC) solution, glycyrrhizin (0.2%) cystein (0.1%) and glycine (2) was attributed to the steroid ring in glycyrrhizin (Fujisawka K. et al., Asian Med. J. (Japan) 23,10 1980). Dosages of SNMC as high as 60 ml/day (~12 mg/dy of glycyrrhizin) have been reported (Iwamura K., Therapiewoche (W. Germany) 30,34 1980).

Inactivation of viruses, in vitro, under certain conditions, has been reported (see, e.g., Pompei R., Exprientia (Switzerland) 36/3 1980). Such anti-viral activity as GTPD compounds sometimes exhibit has been attributed to reverse transcriptase-inhibitory activity (Nakashima, H. et al., Jpn. J. Cancer. Res. 78,8 1987) and to enhancement of interferon-gamma production (Shinada, M. et al., Proc. Soc. Exp. Biol. 181,2 1986), but the exact mechanism of the anti-viral function has not been confirmed.

Dargan, D. J., and Subak-Sharpe, J. H., (J. Gen. Virol., 1985-1986) reported antiviral action of carbenoxolone and cicloxolone on herpes simplex virus. Their dose-response experiments showed cicloxolone sodium or carbenoxolone sodium interfered with the HSV replication cycle and reduced the infectious virus yield by 10,000- to 100,000-fold, cicloxolone being the more potent anti-herpes agent, but no consistent effect on HSV DNA synthesis was identified. Some inhibition of cellular DNA synthesis was observed, but this was relatively slight.

Csonka, G. W. and Tyrrell, D. A. (Br. J. Vener. Dis. 1984, 60 (3) p178) undertook a double blind clinical study to compare the efficacy of carbenoxolone and cicloxolone creams with placebo in initial and recurrent herpes genitalis and reported significant differences in the time to disappearance of pain and the healing of lesions using cicloxolone, but carbenoxolone showed insignificant beneficial effect.

GTPDs have also been evaluated therapeutically as anti-viral agents in the chemotherapy of acquired immune deficiency syndrome (AIDS) (Ito, M., Yamamoto, N., Yakaguaku Zasshi (Japan) 188,2 1988), treatment of Epstein-Barr virus (EBV) infections (Van Benschoten, M. M., Am. J. Acupunct, 16,1 1988) and in the treatment of chronic hepatitis (Fujisawa, K. et al., Asian Med. J. (Japan), 23,10 1980).

The anti-viral activity of GTPDs varies so unpredictably as to preclude any generalized statements as to whether such compounds have general anti-viral effect or even as to whether such compounds will generally have anti-viral value as to any given virus. While GTPD drugs do, in some environments and under some conditions, exhibit some activity against some viruses, no anti-viral therapy based on GTPDs or in vitro antiviral application of GTPDs has been generally accepted. The AIDS-causing viruses, HIV-I and HIV-II, are the first retroviruses identified as pathogenic in man. While HIV are more fragile than most infectious viruses and are susceptible to destruction by most virus-inactivating methods, such as heating, use of detergent compounds, etc., these methods also damage cells, e.g. the red blood cells, and, therefore, are not suitable for use in treating blood. In addition, any substance added to blood will, unless removed, remain in the blood, and must, therefore, be non-toxic when administered intravenously. Removal of added toxins from blood is, at best, complex and expensive and may not be feasible or possible without serious damage to blood components.

The addition of detergents to various blood fractions has been described. My European Patent Specification 0 050 061, published Dec. 11, 1985, in which the term "detergent" is equated with the term "amphophil" to encompass cationic, anionic and nonionic detergents, describes the addition of various detergents to plasma protein products and suggests the addition thereof to other blood derivative products to inactivate virus and for other purposes, followed by the removal of the detergent from the product. High concentrations of detergents, from 0.25 to 10%, were required the process described in the European patent specification.

Bosslet and Hilfenhause, European Patent Specification 0 278 487, discloses that high concentrations of selected detergents inactivate certain envelope viruses.

Neurath and Horowitz, e.g. U.S. Pat. Nos. 4,540,573, 4,481,189, and 4,591,505, indicate, however, that detergent alone is not effective as an antiviral agent in blood plasma and related products. In spite of these teachings, however, it seems safe to conclude that at least some classes of detergents in high concentrations in some types of blood derivatives do have some inactivating effect. The extent and efficacy of such procedures seems open to considerable doubt, however.

The major constituent of plasma is albumin whose primary role is that of osmotic regulation; it is responsible for 75–80% of the osmotic pressure of plasma. Albumin also serves important roles in the transport of small molecules such as drugs.

An important feature which segregates albumin from other colloids as well as crystalloids is its unique ability to bind reversibly with both anions and cations; hence, albumin can transport a number of substances including fatty acids, hormones, enzymes, dyes, trace metals, and drugs. Substances which are toxic in the unbound or free state are generally not toxic when bound to albumin. This binding property also enables albumin to regulate the extracellular concentration of numerous endogenous as well as exogenously administered substances.

Albumin in general has three types of binding sites (one for acidic, one for basic, and one for neutral compounds), and it plays a critical role in the binding and transport of lipid and lipid-soluble material. Albumin binds with and transports many administered drugs. Because of the phenomenon of mutual displacement of similar type substances, adverse drug interactions may occur. This phenomenon may have important ramifications during disease states such as sepsis, burn injury, and circulatory shock due to a number of etiologies, especially in conjunction with treatment with drugs which may be toxic at high concentrations.

Human serum albumin is believed to be a scavenger of oxygen-free radicals, an important phenomenon which also extends to scavenging of radicals required for lipid peroxidation.

Albumin is a potent scavenger of oxygen radicals. Concentrations of human serum albumin below those present in normal human plasma completely inhibit the inactivation of $\alpha_1$-antiproteinase ($\alpha_1$-proteinase inhibitor [$\alpha_1$-PI], $\alpha_1$-antitrypsin) by hypochlorous acid.

Preliminary work in the endotoxemic sheep adult respiratory distress syndrome (ARDS) model also demonstrated that pretreatment with human serum albumin markedly attenuates the 300% to 400% increases in pulmonary lymph flow, transvascular protein clearance, and transvascular protein flow which normally occurs during endotoxemia. UNIQUE FEATURES OF ALBUMIN: A BRIEF REVIEW, Thomas E. Emerson, Jr., Ph.D., *Critical Care Medicine*, Vol. 17, No. 7 (1989).

Treatment with human serum albumin to bind toxic products generated during inflammatory disease states has not received widespread attention. However, a few studies and the inherent ability of albumin to bind with numerous toxic plasma substances support the concept.

Albumin is critical for the transport of numerous compounds, especially non-water soluble ones. It binds with iron and lipids and other potentially toxic substances, e.g., bilirubin. This albumin acts as a buffer to prevent increases in potentially cytotoxic endogenous lipid-soluble substances by binding with, and thus limiting, increases in plasma and interstitial fluid concentrations of these substances.

In addition to displacement of on albumin-bound drug by another, endogenous substances may also alter significantly the unbound or "free" plasma and interstitial fluid concentration of a drug. For example, as the concentration of bilirubin increases in certain disease states, a drug which occupies the same binding site as bilirubin will be displaced by the bilirubin, and the plasma concentration of the free drug will increase, possibly to toxic levels. Also, as the plasma concentration of albumin decreases, the plasma and interstitial fluid concentration of the unbound (free) drug will increase.

It is known that albumin binds to glycyrrhizic triterpenoids. Carbenoxolone is a potent ulcer-healing drug which is extensively bound to plasma proteins and therefore has the potential for displacement interaction. Carbenoxolone has been shown to be bound to human serum albumin in vitro at a different class of binding site to many other drugs and does not potentiate the pharmacological activity of warfarin, tolbutamide, chlorpropamide or phenytoin in the rat. Thornton PC; Papouchado M; Reed PI *Scan J. Gastroenterol Supp* 1980, 65 p35-9.

The binding of glycyrrhizin to human serum and human serum albumin (HSA) was examined by an ultrafiltration technique. Specific and nonspecific bindings were observed in both human serum and HSA. The association constants (K) for the specific bindings were very similar: $1.31 \times 10^5 M^{-1}$ in human serum and $3.87 \times 10^5 M^{-1}$ in HSA. Glycyrrhizin binds to only the albumin fraction. It was concluded that the glyrrhizin-binding sites in human serum exist mainly on albumin and glyrrhizin binds to specific and nonspecific binding sites at lower and higher concentrations than approximately 2 mM, respectively. Ishida S; Sakiya Y; Ichikawa T; Kinoshita M; Awazu S, Chem Pharm Bull (Tokyo) 37 (1). 1989. 226-228.

Comparison by equilibrium dialysis of plasma protein binding sites for carbenoxolone in people under 40 yr of age and in people over 65 yr of age showed that the number of binding sites was reduced in the elderly and this fall was associated with a reduction in plasma albumin levels. Hayes M J; Sprackling M; Langman M, *Gut* 18 (12) 1977 1054-1058.

Albumin has been used as an emulsion stabilizer oil-and-water emulsion injectable medical preparations, e.g. fluorbiprofen, Mizushima et al U.S. Pat. No. 4,613,505, Sep. 23, 1966; as a binding molecule for tryptophan, Pollack U.S. Pat. No. 4,650,789, Mar. 17, 1987; with chemical modification as complexing agents for cholesterol derivatives, Arakawa U.S. Pat. No. 4,442,037, Apr. 10, 1984; as conjugates with enzyme chemically linked to an antibody, Poznansky U.S. Pat. No. 4,749,570, Jun. 7, 1988; and as chemically coupled conjugates of leukotrienes, Young, et al U.S. Pat. No. 4,767,745, Aug. 30, 1988.

Human serum albumin is a remarkable protein which performs numerous tasks critical to maintenance of the milieu interieur. The best known functions of albumin involve regulation of transvascular fluid flux and hence, intra and extravascular fluid volumes and transport of lipid and lipid-soluble substances. However, it is also involved in a number of other vital functions, some of which have only recently been suggested and perhaps others which are as yet unrecognized. Among recognized unique features of albumin are: a) binding, and hence, inactivation of toxic products; b) regulation of the plasma and interstitial fluid concentrations of endogenous and exogenously administered substances and drugs; c) involvement in anticoagulation; d) maintenance of microvascular permeability to protein; and e) scavenging of free radicals and prevention of lipid peroxidation. This latter property may prove to be critically important, particularly in inflammatory disease states in which free radicals are thought to be a major culprit in direct damage due to tissue oxidation and indirect tissue damage due to inactivation of important antiproteinases such as $\alpha_1$-PI and AT-III. See UNIQUE FEATURES OF ALBUMIN: A BRIEF REVIEW, Thomas E. Emerson, Jr., Ph.D., *Critical Care Medicine*, Vol. 17, No. 7 (1989).

The major hazard in producing fractions from large pools of plasma is the transmissions of virus, the most serious, being hepatitis. This is a danger both for the recipient of the fractions and for the workers in fractionation plants. It has been shown that fractionation workers, particularly those engaged in the preparation of plasma pools, are at high risk of developing hepatitis B. The high risk products are fibrinogen, AHF, and prothrombin complex. The low risk products are ISG, PPF, and albumin. The lack of infectivity of PPF and albumin is attributable to heating the final products at 60° C. for 10 hours.

It is now required in the United States that all donors of blood or plasma be tested for the presence of hepatitis B surface antigen by radioimmunoassay or reversed passive hemagglutination. This screening reduces but does not prevent the transmission of hepatitis B virus. A major problem is the transmission of non-B hepatitis, for which there is not screening test. Recent evidence indicates that non-A, non-B hepatitis also invokes a viral agent.

Another hazard of plasma fractionation is the partial denaturation of some fractions such as ISG, caused by the fractionation methods. These denatured proteins may have toxic effects or may be immunogenic in the recipients. Among these undesirable side effects is the significant degree of loss of biological competence and the loss or blockage of many binding sites on albumin are lost by the inherent denaturation resulting from this pasteurization or heating process. According to present technology, the disadvantages of denaturation are more than compensated for by the increased stability and potency of concentrated fractions, but there remains a great need for a fully bio-competent albumin.

The safest source of albumin, in many instances, is the patient's own blood, and it is known to remove the blood, accomplish a partial fractionation of the blood, treat one fraction of the blood and return the treated fraction to the patient. Ishizaki et al U.S. Pat. No. 4,839,055, Jun. 13, 1989, describe a method for treating a blood which involves separating the blood withdrawn from a patient's body, mixing the condensed blood and the low molecular weight protein with a substitute liquid and returning the combined liquid into the patient's body.

SUMMARY OF THE INVENTION

The present invention comprises methods inactivating viruses in blood plasma by the use of extracts of the well-known flavoring agent licorice, referred to here as glycyrrhizinic triterpenoids or GTPD compounds.

Glycyrrhizic acid, 20B-carboxy-11-oxo-30-norolean-12-en-3B-yl-2-O-B-D-glucopyranuronsyl-$\alpha$-D-glucopyranosiduroinic acid, commonly known as glycyrrhizin, glycyrrhizinic acid or glycyrrhetinic acid glycoside (also referred to as biosone, enoxolone, and glycyrrhetin) an extract from Glycyrrhiza, better known as licorice, an extract of the dried rhizome and roots of Glycyrrhiza glabra, is a triterpene and is exemplary of the triterpenes to which this invention relates. Analogous triterpenes to which this invention relates include carbenoxolone and cicloxolone. This invention thus relates to glycyrrhizinic acid and analogues thereof, in the form of acids, salts, esters and other derivatives. Many such derivatives are known, such as, for example, glycyrrhetinyl stearate; monopotassium glycyrrhetin; potassium glycyrrhetinate; 11-deoxyoglycrrhetinic acid hydrogen maleate sodium salt; $\alpha$-D-glucopyranosiduronic acid monoarginine glycyrrhizinate; 18$\alpha$-Glycyrrhizic acid monosodium salt; 18-$\alpha$-Glycyrrhizic acid monopotassium salt; disodium 18-$\alpha$-glycyrrhizate; glycyrrhizinic acid mono(triethanolamine) salt; trisodium glycyrrhizinate; sodium glycyrrhizate; ammonium glycyrrhizinate; sodium carbenoxolone (biogastrone; glycyrrhetinic acid hydrogen succinate disodium salt); and acetylglycyrrhetic acid (glycyrrhetinyl acetate). Glycyrrhizin and the virucidal analogues and derivatives thereof are referred to for convenience herein as glycyrrhizic triterpendoids abbreviated GTPD. Presently the principal GTPD compounds of interest are glycyrrhizin (coded TPD-1 in some of my work), carbenoxolone (coded TPD-2 in some of my work) and cicloxolone.

Ring-substituted derivatives of GTPD compounds are contemplated and are included in this invention. Halogen ring substituents, such as, for example, fluoro- and chloro- substituents, sulfate and other active and/or inactivating substituents to the ring structure of GTPD compounds are specifically included in this invention, without excluding other ring-substituted derivatives of GTPD compounds.

This invention, thus, relates to methods for collecting and treating blood plasma with GTPD compounds, e.g. glycyrrhizic acid, its analogues such as carbenoxolone and cicloxolone, analogues thereof and the salts, esters and other derivatives thereof, and to blood plasma for transfusion containing such compounds which is free of HIV virus capable of infecting the donee of such plasma. Inactivation of other viruses to a greater or lesser extent also results.

Viral inactivation, as used here, means rendering the virus non-infective, i.e. the virus does not induce disease in a patient. In most instances traditional methods of quantifying virus population growth and reduction, e.g. log kill (See Fraenkel-Conrat, H., Kimball, P. C., and Levy, J. A. VIROLOGY, Second Edition, Prentice Hall, Englewood Cliffs, N.J., 1988, and Jakoby, W. H. and Pastan, I. H. (Eds), CELL CULTURE, (Volume LVIII of "Methods in Enzymology", Academic Press, Inc., New York, Chapter 11) are good indicators of viral inactivation. However, viral inactivation is accomplished by GTPD-Albumin beyond the log kill measurement since any remaining virus are incapable of infecting a patient and are incapable of replicating.

The present invention is also embodied in blood plasma which comprise one or more glycyrrhizic triterpenoid compounds in an amount of from 0.0001 to 10 wt/%, preferably about 0.1 to about 3 wt/%, and glycerol in very low concentrations of from approximately 0.0001 wt/% to 5 wt/%, preferably 0.0001 to 0.01 wt/%. There is a striking synergism between the glycerol and the glycyrrhizic triterpenoid compound(s) rendering the combination surprisingly effective in inactivating susceptible viruses which may be in the sample.

The present invention is also embodied in blood plasma which comprises one or more glycyrrhizic triterpenoid compounds in an amount of from 0.0001 to 10 wt/%, preferably about 0.1 to about 3 wt/%, and EDTA in very low concentrations of from approximately 0.0001 to 5 wt/%, preferably 0.0001 to 0.01 wt/%. There is a striking synergism between the EDTA and the glycyrrhizic triterpenoid compound(s) rendering the combination surprisingly effective in inactivating susceptible viruses which may be in the sample.

The present invention is also embodied in a method of inactivating virus in plasma by adding, at any stage, directly or indirectly, to the plasma an amount of the GTPD compound, e.g. glycyrrhizin, glycyrrhetinic acid, carbenoxolone or cicloxolone in combination with albumin, the combination being referred to as GTPD-Albumin, sufficient to inactivate CMV and/or other viruses in the plasma such that the GTPD comprises from about 0.001 weight/percent (w/%) to about 10 w/%, generally in the range of about 0.05 to about 3 w/%, of plasma, and to plasma containing GTPD-Albumin.

The present invention is also embodied blood plasma which comprise, one or more glycyrrhizic triterpenoid compounds in an amount of from 0.0001 to 10 wt/%, preferably about 0.1 to about 3 wt/%, and a detergent, preferably a nonionic detergent such as Tween ® and Triton X-100 ® in very low concentrations of from approximately 0.0001 to 5 wt/%, preferably 0.0001 to 0.01 wt/%. There is a striking synergism between the detergent and the glycyrrhizic triterpenoid compound(s) rendering the combination surprisingly effective in inactivating susceptible viruses which may be in the sample.

It is significant to note that the concentration levels of detergent which are suitable in this invention have little antiviral effect but when used in combination with glycyrrhizic triterpenoid compounds, increases the antiviral effectiveness very dramatically, resulting in as much as 1 to 3 logs higher inactivation than result with the same concentration of the glycyrrhizic triterpenoid compounds alone at the same concentration.

This invention is also embodied in a composition of matter consisting essentially of blood plasma which contains an amount of GTPD compound consisting essentially of glycyrrhizin, carbenoxolone, cicloxolone analogues and derivatives thereof, or mixtures thereof effective to inactivating CMV and/or other viruses.

This invention relates to methods for collecting and treating blood plasma with GTPD compounds, e.g. glycyrrhizic acid, its analogues such as carbenoxolone and cicloxolone, analogues thereof and the salts, esters and other derivatives thereof, and to blood plasma for transfusion containing such compounds which is free of CMV virus capable of infecting the donee of such plasma. Inactivation of other viruses also results.

At least one of the retroviridae is susceptible to the treatment of this invention, according to presently available data. The most notorious of the retroviridae, HIV-1, the only virus thus far identified as inducing AIDS in humans, is inactivated and/or killed using the methods and compositions of this invention. Other retroviridae are considered to be susceptible to the present invention, and treatment to prevent transmission of retrovirus-infected organs, tissues, cell and fluids is within the scope of this invention.

In summary, this invention is embodied in commercial products comprising blood plasma comprising an amount of a GTPD compound consisting essentially of glycyrrhizin, carbenoxolone, cicloxolone analogues and derivatives thereof, or mixtures thereof, alone or in combination with albumin, glycerol, ethylene diamine tetraacetic acid, or detergent, effective to inactivate CMV and/or other viruses and methods of preparing the same. Such products may be stored, shipped, sold and used in transfusions.

DESCRIPTION OF THE PREFERRED EMBODIMENT

The preferred method of carrying out the invention comprises mixing one or more GTPD compounds, e.g. glycyrrhizin, carbenoxolone or cicloxolone with plasma, or with blood before plasma separation, to comprise from about 0.0001 weight/percent (w/%) to about 10 w/%, generally in the range of about 0.05 to about 3 w/%, of the blood plasma, such amount being sufficient to inactivate CMV and/or other viruses in the plasma.

The plasma, or blood if the glycyrrhizic triterpenoid compounds are added before plasma separation, is held for a sufficient period of time, e.g. 15 minutes or more, at normal room temperatures or for an hour or more at near 0° C. to assure that CMV is inactivated before the plasma is administered by transfusion to the donee patient or fractionated for blood products.

In carrying out this method, conventional blood plasma preparation and handling procedures, as modified by the addition of glycyrrhizic triterpenoid compounds. The handling and administration of the plasma by transfusion is the same as is conventionally carried out, save only for the processes involving preparation of the plasma to contain the GTPD compounds.

Of the readily available GTPD compounds, carbenoxolone is preferred for its anti-viral effectiveness; however, carbenoxolone solutions are not stable for long periods of time and should be used freshly prepared.

Contrary to what some reports of anti-viral activity may suggest, cicloxolone is less effective than carbenoxolone as an anti-viral agent in blood plasma. On the other hand, however, cicloxolone and glycyrrhizin are stable over relatively long periods of time in solution.

The GTPD compounds may be used in their acid form, as plasma is a very potent buffer; however, it is always necessary to check the pH after adding the GTPD compound and, if necessary, adjust the pH to about 7.0–8.0, e.g. with NaOH or KOH, before using the plasma, as certain acid form GTPD compounds drop the pH of plasma significantly to the pH 4–5 range.

The acid form of the GTPD compounds is only slightly soluble in water but is quite soluble in dimethyl sulfoxide. The salt, e.g. ammonium, sodium or potassium salts, of the GTPD compounds are, generally, soluble in water, the sodium and potassium salts being more soluble than the ammonium salts. It is, thus, convenient to purchase or prepare the GTPD compounds as sodium or potassium salts.

Of very great importance, it has been discovered that plasma treated as described above, when fractionated to produce plasma, clarifies the plasma, eliminating the translucence characteristic of most plasma. Additionally, the addition of the glycyrrhizic triterpenoid compounds of this invention to plasma followed by centrifugation clarifies the plasma.

Further, standard serum analyses, e.g. serum protein electrophoresis, basic plasma chemistry tests, and lipid tests were unaffected by the presence of the GTPD additives of this invention.

Thus, according to this invention, by a one-step addition of one or more GTPD compounds to plasma at or after the time of collection and before or after plasma-cell separation, CMV and other blood-borne viruses, e.g. HIV, are killed or inactivated, plasma is clarified, and conventional plasma analysis are not significantly effected.

The invention is embodied in an article of commerce comprising packaged transfusion blood plasma in a container of human blood plasma containing one or more glycyrrhizic triterpenoid compounds in an amount of from 0.0001 to 10 wt/%, preferably from about 0.5 to about 3 wt/% effective to substantially inactivate at least cytomegalovirus.

As a method of treating a patient, the invention is a process comprising transfusing the patient with blood plasma comprising one or more glycyrrhizic triterpenoid compounds in a concentration of from 0.0001 to 10.0 wt/%, preferably from about 0.5 to about 3 wt/%, based on blood plasma, sufficient to substantially inactivate at least CMV.

GTPD-Albumin significantly enhances the effectiveness of the GTPD when added, in lieu of or in addition to GTPD alone, at any stage, directly or indirectly, to the plasma. An amount of the GTPD compound, e.g. glycyrrhizin, glycyrrhetinic acid, carbenoxolone or cicloxolone in combination with albumin, the combination being referred to as GTPD-Albumin, is added sufficient to inactivate CMV and/or other viruses in the plasma such that the GTPD comprises from about 0.001 weight/percent (w/%) to about 10 w/%, generally in the range of about 0.05 to about 3 w/%, of plasma.

Albumin from any source which is safe for intravenous use may be used to form GTPD-Albumin for use in this invention. Conventional caprylate stabilized, heat treated albumin may be used, for example. GTPD-Albumin is prepared simply by mixing GTPD into an albumin solution and allowing the solution to equilibrate a sufficient period of time, a few minutes being sufficient, to assure homogeneity and the formation of GTPD-Albumin. It is convenient to form a saturated solution of GTPD-Albumin, allow it to stand overnight and, if necessary, to filter the solution to assure than any excess GTPD or any precipitate is removed, and then to dilute the GTPD-Albumin solution as desired, or use it full-strength as an additive to blood plasma.

In appropriate instances, the patient's own albumin may be used. If, for example, it is known sufficiently in advance that a patient will be receiving blood plasma, and if the patient's health permits, an appropriate amount of the patient's blood may be taken and fractionated sufficient to provide a fraction which does not contain red blood cells, contains the albumin, preferably delipidated albumin, of the patient. GTPD is then mixed into the albumin-containing fraction and the GTPD-Albumin is allowed to form by letting the mixture stand for a few minutes to a few hours. Prolonged standing or storage, e.g. several days to a few weeks, is not detrimental. The GTPD-Albumin is then mixed with the blood or blood plasma and the mixture is maintained at a suitable temperature long enough, as discussed above, to inactivate the virus which may be in the blood or plasma. For example, GTPD-Albumin may be prepared the day preceding or a few hours before elective surgery using the patient's own albumin. The GTPD-Albumin is mixed with the transfusion blood plasma about an hour before expected use thereof and the GTPD-Albumin-blood plasma mixture is maintained at about 37° C.±about 8° C. for an hour or more and the virus-inactivated blood plasma is used to transfuse the patient.

Particularly striking results are accomplished using albumin which has not been stabilized in the traditional way, e.g. with caprylate, and has not been heated. According to the prior art, such an albumin product would be regarded as unsafe because of the potential presence of pathogenic virus. If, however, the stabilization step and the heating step are replaced by the addition of GTPD to the albumin, the virus are inactivated and the albumin is biologically competent. GTPD-Albumin formed in this manner has higher biological activity than GTPD-Albumin prepared from conventional albumin. In a test using a VSV/BVD sensitive cell line performed when the cells were in log phase, the samples were inoculated with $10^9$ pfu of vesicular stomatitis virus (VSV), incubated overnight and serially diluted in MEM with 10% FBS (fetal bovine serum), and then inoculated with VSV. The 0.01% GTPD (carbenoxolone) alone and 0.10% GTPD (carbenoxolone) in 5% solutions of various albumins were introduced at dilutions of from $1:10^2$ to $1:10^9$. The cells were examined daily for five days for virus caused CPE. Following table summarizes the comparative results.

| LOG KILL OF VSV BY TPD | |
|---|---|
| Albumin Used | Log Kill Five Days |
| None | 4.6 |
| Baxter Buminate ® (USP Lot 2746M011AA) | 1.3 |
| Miles Human Albumin Fatty Acid Free (Lot 82-324) | 1.6 |
| Hyland IS 9988 Human Albumin | 2.0 |
| Non-Stabilized, solvent detergent albumin[1] | 5.6+ |

[1]Human serum albumin prepared by Cohn Fractionation, Solvent-Detergent precipitation and alcohol ultrafiltration, not heated and no stabilizer, e.g. caprylate or tryptophan added.

It should be noted that at extreme dilutions of GTPD, bind to albumin may actually reduce antiviral activity; however, higher concentrations of GTPD can be used and the viral inactivation is not decreased even with the least biologically competent albumin and enhancement is generally observed.

Non-stabilized, non-heated albumin is, however, vastly superior to "conventional", i.e. stabilized and pasteurized, albumin, presumably because of a greatly increased ability to form GTPD-Albumin as a result of greater biological competence. Even at extreme dilution, an approximately 6 log kill was found. At lower dilutions (higher concentrations of GTPD) the kill was apparently complete, probably 7 to 9 logs.

It has also been found that the deactivation of antiviral power of GTPD by lipoproteins and/or fatty acids is eliminated or greatly reduced by adding the GTPD as GTPD-Albumin. It is important, therefore, that the GTPD-Albumin be formed using delipidated albumin, to obtain maximum effect with minimum concentration. If, for example, it were desired to add GTPD to plasma from which lipids and lipoproteins had not been removed, it would be of importance, using the albumin enhancement, to prepare GTPD-Albumin before addition and add the GTPD as GTPD-Albumin. On the other hand, if the plasma has been delipidated, GTPD-Albumin can be added directly to the plasma.

The ability of albumin to (a) bind GTPD, (b) not reduce and generally to enhance the viral inactivation power of GTPD, and (c) eliminate at low concentrations or greatly reduce any tendency of GTPD to hemolyze red blood cells is of enormous import. These results mean that GTPD can be carried into the system via albumin without losing its viral inhibition power, can be used at much higher concentrations than would otherwise be possible, and can be used where hemolysis is unacceptable.

As reported in the prior art, it is known that GTPD will bind to albumin. The nature of the binding, which results in GTPD-Albumin, is not fully understood. GTPD bound to albumin would be expected to be less active chemically and biologically. Quite surprisingly, however, it was found that the viral inactivation characteristics of GTPD bound to albumin were not only not decreased but were, in some instances at least, enhanced.

In all embodiments, the invention exhibits a number of surprising results. The spotty results reported in efforts to determine if, and to what extent, GTPD compounds are indeed virucidal agents led the art to believe, as has been reported, that "the likelihood of developing a blood additive that would kill HIV and HBV and have no effect on laboratory examination of blood plasma seems small." (Peter C. Fuchs, M. L. O., Oct. 13, 1988). In addition, notwithstanding the prior art in which anti-viral activity, to the extent it exists, of GTPD compounds is uncertain, unpredictable and, as yet, unexplained, and the widely accepted proposition that no blood and blood plasma additive could be found which would inactivate blood-borne viruses without adversely effecting the blood and blood plasma, e.g. lysing the red blood cells and/or interfering with blood and blood plasma analyses, the present invention embodies a processes and blood plasma compositions in which these desired but hitherto unattainable results are accomplished.

Carbenoxolone, alone, at a concentration of 0.01 wt/% was compared with carbenoxolone was compared with 0.01 carbenoxolone containing, respectively, 0.00025, 0.005 and 0.01 wt % of glycerol, and, in another test, with 0.0005, 0.001 and 0.002 wt % detergent, TRITON X-100®. The test used a VSV/BVD sensitive cell line (EBtr=embryonic bovine tracheal fibroblast). The test was performed when the cells were in log phase to optimize virus-caused CPE. The samples were inoculated with $10^9$ pfu of VSV and incubated. The samples were then serially diluted with MEM with 10% FBS to reach a 9-fold dilution of the virus. The serial dilutions were inoculated in quadruplicate wells (24 well plate of Ebtr cells) and inoculated at 37° C. VSV kill was increased by the addition of glycerol or the detergent, except that extremely dilute solutions of glycerol did not give a significant enhancement of virus inactivation.

Thus, it has been established that an exemplary triterpenoid compound, carbenoxolone, glycyrrhizin and cicloxolone, as well as glycyrrhizic acid and derivatives thereof, typically in the form of salts, in a concentration range of from about 0.001 to 0.005 to 10 wt/% when combined with one or more enhancers, e.g. glycerol, detergent, EDTA or albumin, in the range of from 0.001 to 0.0001 to 5 wt/%, preferably under an 0.001 to 0.01 wt/%, greatly accelerates the inactivation of virus and increases the ultimate inactivation, typically by at least 1 log and as high as 3 logs.

Solutions of glycyrrhizic compounds in the range of from about 0.1 to about 2 or 3 wt/% are presently considered optimal as to concentration, lower concentrations of glycyrrhizic compounds being possible when combined with detergent.

The full scope of types of detergents which may be used in this invention has not been fully determined. The essential requirements are that the detergent have a high detergency action and not interfere with the laboratory tests, at the level of addition involved.

The preferred detergents are classed as nonionic detergents, examples of which include: polyoxyethylene-based detergents such as TWEEN® and octyl phenoxy polyethoxy ethanol-based detergents such as TriTON X-100®, which are preferred, and detergents based upon polyethylene glycol and condensation polymers of ethylene oxide and propylene glycol. These are, of course, merely examples of some of the more common classes of detergents suitable for use in this invention and other classes of nonionic detergents may be used.

Ionic detergents such as, for example, sodium lauryl sulfonates, may also be used, but is may be necessary to make adjustments in the laboratory procedures or results to compensate for the addition of components of the detergent.

A comparison of results using GTPD compounds alone by adding from approximately 0.0001 to 5 wt/%, preferably 0.001 to 1.0 and to 0.0001 to 0.1 wt/% detergent to accomplish virus inactivation, two results were striking. First, inactivation adequate for most purposes, e.g. 2-4 log kills, could be obtained in a fraction of the time previously required. Secondly, the ultimate inactivation was increased by a minimum of 1 log in most cases and typically up to 3 logs, or more, in some instances.

The result was particularly surprising in view of the general lore of the art that low levels of detergent have little or inadequate anti-viral effects. Quite clearly, there is more here than a mere additive effect, since the GTPD effect plus a negligible or zero effect would have been predicted. It is speculated that in some way the detergent renders the cell membrane more accessible to GTPD, which is believed to attach to the membrane but which as no detergency of consequence. This is, however, only a speculation, and there is no hard evidence to support an elucidation of the mechanism of action.

The speed of action and ultimate inactivation achievable using GTPD alone or with detergent is also significantly increased by maintaining the blood plasma at approximately body temperature, 27° C. or higher, up to 40°-45° C., preferably, or up to 60° C. if desired to accelerate inactivation or for other reasons.

Unlike the prior art, it is not necessary to remove the very small, trace amounts of non-toxic detergent which is sufficient for the present invention. This feature, alone, is of very significant economic and practical importance.

Solutions of glycyrrhizic compounds in the range of from about 0.01 to about 2 or 3 wt/% are presently considered optimal as to concentration, lower concentrations of glycyrrhizic compounds being possible when combined with glycerol.

A comparison of results using GTPD compounds alone and GTPD modified by adding from approximately 0.0001 to 5 wt/%, preferably 0.001 to 0.1 wt %, glyceral to blood products, the product of interest being plasma, to accomplish virus inactivation was striking. First, inactivation adequate for most purposes, e.g. 2-4 log kills, could be obtained in a fraction of the time previously required. Secondly, the ultimate inactivation was increased by a minimum of 1 log in most cases and typically up to 3 logs, or more, in some instances.

The result was particularly surprising in view of the general lore of the art that low levels of glycerol have little or inadequate anti-viral effects. Quite clearly, there is more here than a mere additive effect, since the GTPD effect plus a negligible or zero effect would have been predicted. It is speculated that in some way the glycerol renders the cell membrane more accessible to GTPD, which is believed to attach to the membrane but which as no detergency of consequence. This is, however, only a speculation and there is no hard evidence to support an elucidation of the mechanism of action.

Solutions of glycyrrhizic compounds in the range of from about 0.01 to about 2 or 3 wt/% are presently considered optimal as to concentration, lower concentrations of glycyrrhizic compounds being possible when combined with EDTA.

A comparison of results using GTPD compounds alone or by adding from approximately 0.001 to 5 wt/%, preferably 0.001 to 1 wt/% EDTA to accomplish virus inactivation was striking. First, inactivation adequate for most purposes, e.g. 2–4 log kills, could be obtained in a fraction of the time previously required. Secondly, the ultimate inactivation was increased by a minimum of 1 log in most cases and typically up to 3 logs, or more, in some instances.

Quite clearly, there is more here than a mere additive effect. It is speculated that in some way the EDTA renders the cell membrane more accessible to GTPD, which is believed to attach to the membrane but which as no detergency of consequence. That is, however, only a speculation and there is no hard evidence to support an elucidation of the mechanism of action.

The GTPD compounds can be mixed with other active compounds with synergistic results in inactivation of virus. Such synergistic and potentially synergistic compounds include the anti-viral drug AZT, which is known to act synergistically with the GTPD compounds, dextrans, butyl hydroxy toluene, fatty acids such as oleic acid, chelating agents such as EDTA, and compounds of transition and heavy metals.

INDUSTRIAL APPLICATION

The invention has direct application in the blood banking industry and the blood product industry.

What is claimed is:

1. A method of treating human blood plasma comprising mixing such human blood plasma at the time of sampling with one or more glycyrrhizic triterpenoid compounds in a concentration of from about 0.0001 to about 3 wt/%, and detergent in a concentration of from about 0.0001 to about 5 wt/%, based on the quantity of the human blood plasma, sufficient to substantially inactivate susceptible viruses in said human blood plasma.

2. The method of claim 1 comprising the further step of maintaining the human blood plasma to which glycyrrhizic triterpenoid compound and detergent have been added at a temperature of from about 37° C. to about 60° C. for a period of up to about 24 hours to assure at least a three log inactivation of virus in the human blood plasma.

3. A method of treating human blood plasma comprising mixing such human blood plasma with one or more glycyrrhizic triterpenoid compounds in a concentration of from about 0.0001 to about 3 wt/%, and glycerol in a concentration of from about 0.0001 to about 5 wt/%, based on the quantity of plasma, sufficient to substantially inactivate susceptible viruses therein.

4. The method of claim 3 comprising the further step of maintaining the plasma to which glycyrrhizic triterpenoid compound and glycerol have been added at a temperature of from about 37° C. to about 60° C. for a period of up to about 24 hours to assure at least a three log inactivation of virus in the human blood plasma.

5. A method of treating human blood plasma comprising mixing such human blood plasma with one or more glycyrrhizic triterpenoid compounds in a concentration of from about 0.0001 to about 3 wt/%, and ethylene diamine tetraacetic acid or salts thereof in a concentration of from about 0.0001 to about 5 wt/%, based on the quantity of the human blood plasma, sufficient to substantially inactivate susceptible viruses in said human blood plasma.

6. The method of claim 5 comprising the further step of maintaining the human blood plasma to which glycyrrhizic triterpenoid compound and ethylene diamine tetraacetic acid or salts thereof have been added at a temperature of from 37° C. to about 60° C. for a period of up to about 24 hours to assure at least a 3-log inactivation of virus in the human blood plasma.

7. A method for treating human blood plasma comprising mixing such human blood plasma with a combination consisting essentially of one or more glycyrrhizic triterpenoid compounds in a concentration of from about 0.0001 to about 5 wt/% based on blood product and from about five to about one hundred times that amount of albumin, the concentration being sufficient to substantially inactivate susceptible viruses found in animal fluids and tissues within said time.

8. The method of claim 7 comprising the further step of maintaining the human blood plasma at a temperature of from about 37° C. to about 60° C. for a period of up to about 24 hours to assure at least a 3-log inactivation of virus in the human blood plasma.

9. The method of claim 7 comprising mixing said albumin-glycyrrhizic triterpenoid compound combination in an amount sufficient to form a concentration of glycyrrhizic triterpenoid compounds of from about 0.001 to about 0.05 to about 3 wt/% in the human blood plasma.

10. The method of claim 7 comprising the further step of maintaining the mixture of plasma and glycyrrhizic triterpenoid compounds at a temperature of from about 37° C. to about 60° C. for a period of up to about 24 hours to assure at least a 3-log inactivation of virus in the human blood plasma.

11. The method of claim 7 comprising mixing said glycyrrhizic triterpenoid compounds with the plasma in an amount sufficient to form a concentration of from about 0.001 to about 3 wt/% in the human blood plasma.

12. A method for treating delipidated human blood plasma comprising mixing such human blood plasma with one or more glycyrrhizic triterpenoid compounds in a concentration of from about 0.001 to about 5 wt/% based on blood product to form a combination of glycyrrhizic triterpenoid compound bound to albumin in the plasma, the concentration being sufficient to substantially inactivate susceptible viruses found in animal fluids and tissues within said time.

13. The method of treating a patient comprising: drawing blood from the patient, fractionating such blood sufficiently to form human blood plasma, adding one or more glycyrrhizic triterpenoid compounds to said human blood plasma, and adding the resulting mixture of plasma and glycyrrhizic triterpenoid compounds to transfusion blood, the glycyrrhizic triterpenoid compounds being added in an amount of from about 0.0001 to about 5 wt/%, based on the total of plasma and transfusion blood, sufficient to substantially inactivate susceptible viruses in the transfusion blood transfusing the thus treated blood into a human patient.

14. The method of treating a human patient comprising: drawing blood from the human patient, fractionating such blood sufficiently to form an albumin-containing liquid, adding one or more glycyrrhizic triterpenoid compounds to said albumin-containing liquid, and adding the resulting mixture of albumin-containing liquid and glycyrrhizic triterpenoid compounds to transfusion blood, the glycyrrhizic triterpenoid compounds being added in an amount of from about 0.0001 to about 5 wt/%, based on the amount of transfusion blood, sufficient to substantially inactivate susceptible viruses in the transfusion blood; and infusing the patient's thus treated transfusion blood into said patient.

15. A composition of matter consisting essentially of human blood plasma suitable in quality and quantity for human therapeutic use, one or more glycyrrhizic triterpenoid compounds and a non-toxic amount of detergent.

16. A composition of matter consisting essentially of human blood plasma suitable in quality and quantity for human therapeutic use, one or more glycyrrhizic triterpenoid compounds and a non-toxic amount of glycerol.

17. A composition of matter consisting essentially of human blood plasma suitable in quality and quantity for human therapeutic use, one or more glycyrrhizic triterpenoid compounds and a non-toxic amount of ethylene diamine tetraacetic acid or salts thereof.

18. A composition of matter consisting essentially of human blood plasma, one or more glycyrrhizic triterpenoid compounds and non-stabilized, non-pasteurized albumin.

19. The method of treating a human patient comprising: drawing blood from the human patient, fractionating such blood sufficiently to form human blood plasma suitable in quality and quantity for human therapeutic use, adding one or more glycyrrhizic triterpenoid compounds to said human blood plasma, and adding the resulting mixture of plasma and glycyrrhizic triterpenoid compounds to transfusion blood, the glycyrrhizic triterpenoid compounds being added in an amount of from about 0.001 to about 5 wt/%, based on the total of plasma and transfusion blood, sufficient to substantially inactivate susceptible viruses in the transfusion blood and transfusing the thus treated blood into a human patient.

20. A composition of matter consisting essentially of human blood plasma suitable in quality and quantity for human therapeutic use, one or more glycyrrhizic triterpenoid compounds in a concentration of from about 0.0001 to about 3 wt/% and detergent in a concentration of from about 0.0001 to about 5 wt/%, based on the quantity of human blood plasma, sufficient to substantially inactivate susceptible viruses in said human blood plasma.

21. A composition of matter consisting essentially of human blood plasma suitable in quality and quantity for human therapeutic use, one or more glycyrrhizic triterpenoid compounds in a concentration of from about 0.0001 to about 3 wt/%, and glycerol in a concentration of from about 0.0001 to about 5 wt/%, based on the quantity of human blood plasma, sufficient to substantially inactivate susceptible viruses therein.

22. A composition of matter consisting essentially of human blood plasma suitable in quality and quantity for human therapeutic use, one or more glycyrrhizic triterpenoid compounds in a concentration of from about 0.0001 to about 3 wt/%, and ethylene diamine tetraacetic acid or salts thereof in a concentration of from about 0.0001 to about 5 wt/%, based on the quantity of the human blood plasma, sufficient to substantially inactivate susceptible viruses in said human blood plasma.

23. A composition of matter consisting essentially of human blood plasma suitable in quality and quantity for human therapeutic use, one or more glycyrrhizic triterpenoid compounds in a concentration of from about 0.0001 to about 5 wt/% based on blood product and from about five to about one hundred times that amount of albumin from a source other than the human blood plasma, sufficient to substantially inactive susceptible viruses found in said human blood plasma.

24. Pooled human blood plasma comprising a transfusion container of human blood plasma pooled from multiple donors suitable in quality and quantity for human therapeutic use by reason of it containing one or more glycyrrhizic triterpenoid compounds in an amount of from about 0.0001 to about 10 wt/% effective to substantially inactivate susceptible viruses.

25. The pooled transfusion human blood plasma of claim 24 comprising from about 0.1 to about 3 wt/% glycyrrhizic triterpenoid compounds.

* * * * *